United States Patent
Wilk

(10) Patent No.: US 6,730,014 B2
(45) Date of Patent: May 4, 2004

(54) MEDICAL TREATMENT METHOD AND DEVICE UTILIZING MAGNETIC PARTICLES

(76) Inventor: Peter J. Wilk, 185 W. End Ave., New York, NY (US) 10023

( * ) Notice: Subject to any disclaimer, the term of this patent is extended or adjusted under 35 U.S.C. 154(b) by 65 days.

(21) Appl. No.: 09/755,485

(22) Filed: Jan. 5, 2001

(65) Prior Publication Data

US 2002/0091295 A1 Jul. 11, 2002

(51) Int. Cl.⁷ .................................................. A61N 2/00
(52) U.S. Cl. ............................ 600/12; 600/9; 600/15; 606/151; 606/157; 602/42; 602/78
(58) Field of Search ......................... 600/12, 9, 10, 600/11, 13, 14, 15, 249; 128/898; 606/139, 151, 153, 154, 157, 158; 602/41, 42, 52, 54, 57, 78

(56) References Cited

U.S. PATENT DOCUMENTS

| | | | | |
|---|---|---|---|---|
| 3,986,493 A | * | 10/1976 | Hendren, III | 600/12 |
| 5,176,692 A | * | 1/1993 | Wilk et al. | 606/151 |
| 5,254,113 A | * | 10/1993 | Wilk | 606/153 |
| 5,303,719 A | * | 4/1994 | Wilk et al. | 128/898 |
| 5,330,486 A | | 7/1994 | Wilk | |
| 5,353,786 A | * | 10/1994 | Wilk et al. | 600/249 |
| 5,895,404 A | * | 4/1999 | Ruiz | 606/151 |
| 6,231,496 B1 | * | 5/2001 | Wilk et al. | 600/9 |
| 6,296,604 B1 | * | 10/2001 | Garibaldi et al. | 600/12 |
| 6,315,709 B1 | * | 11/2001 | Garibaldi et al. | 600/12 |
| 6,364,823 B1 | * | 4/2002 | Garibaldi et al. | 600/12 |
| 6,398,713 B1 | * | 6/2002 | Ewing et al. | 600/9 |

* cited by examiner

Primary Examiner—Henry Bennett
Assistant Examiner—Fadi H. Dahbour
(74) Attorney, Agent, or Firm—R. Neil Sudol; Henry D. Coleman; William J. Sapone

(57) ABSTRACT

In a medical treatment method, magnetic elements are injected into organic tissues of a patient. The magnetic elements are disposed, upon injection, on opposite sides of tissues or a hole to be closed or collapsed. Owing to magnetic attraction between the magnetic elements, the organic tissues of the patient are drawn together to constrict tissues or to close or collapse a wound or vessel.

17 Claims, 6 Drawing Sheets

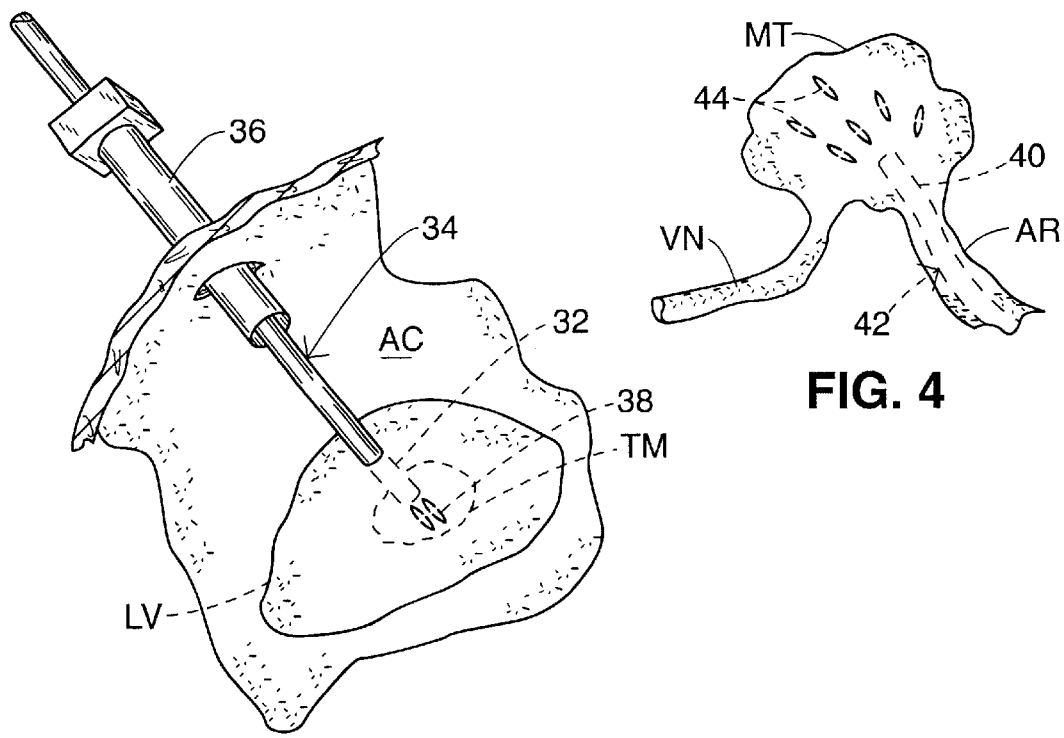
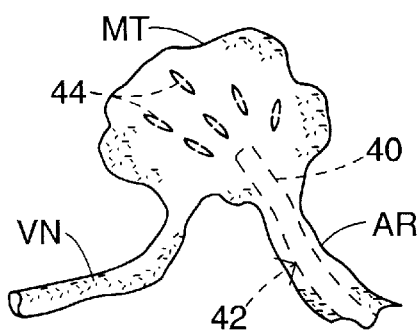
FIG. 3
FIG. 4
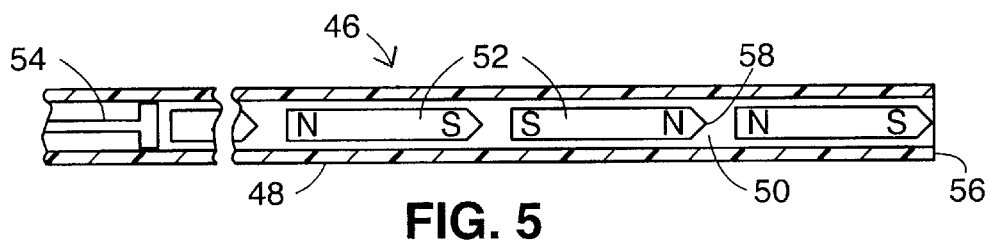
FIG. 5
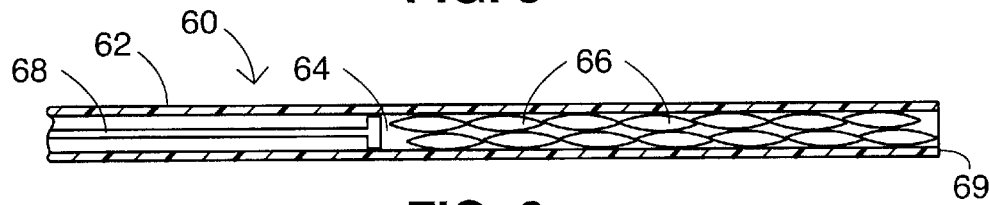
FIG. 6
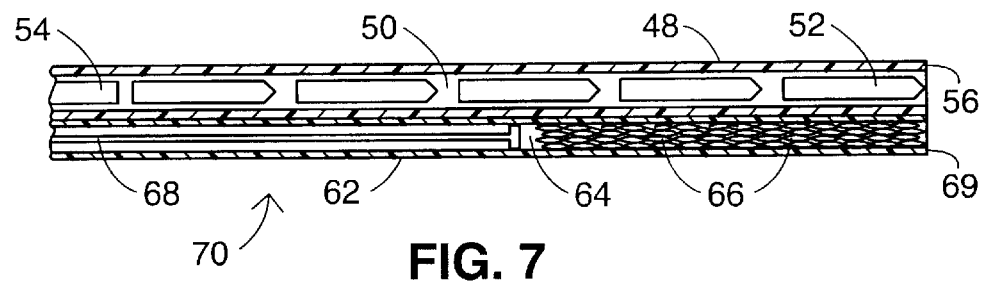
FIG. 7

MEDICAL TREATMENT METHOD AND DEVICE UTILIZING MAGNETIC PARTICLES

BACKGROUND OF THE INVENTION

This invention relates to a medical treatment method and an associated device. The method may be used in the treatment of such conditions as esophageal varices, hemorrhoids, tumors, and wounds or holes particularly in internal tissues.

Many medical conditions involve swollen tissues which attain such a size as to inhibit or interfere with one or more necessary physiological functions. An example of such swollen tissues are varices of the digestive tract. Gastric and esophageal varices are a devastating complication of portal hypertension. To treat such bleeding varices, it is necessary at times to use a long tube with two inflatable balloons at a distal end, known as a "Blakemore Tube." In using this device to stop the flow of blood in the stomach, the tube is blindly inserted into the esophagus until it is believed that the most distal of the two balloons is located in the patient's stomach. That balloon is then inflated and the tube placed in tension (e.g., via attachment to a weight outside of the patient) to pull the inflated balloon against the stomach wall at the gastroesophageal junction. In the event that bleeding esophageal varices are to be treated, the relatively proximal balloon is also inflated.

The rate of complications in the use of the Blakemore tube is immense. The complications result mainly from poor placement or slippage of the tube. In addition, the relatively proximal balloon sometimes erodes into the esophagus, causing bleeding, perforation and necrosis of the esophagus.

Another kind of swollen internal tissues, namely, hemorrhoids, are located at the downstream end of the digestive tract. Hemorrhoids are a common malady which causes substantial pain and suffering to millions of people. The best conventional treatment for this affliction is a soaking of the hemorrhoidal tissues in a hypertonic bath, such as a solution of Epsom salts. However, this treatment is not especially effective. A need exists for a more convenient and yet effective treatment for hemorrhoids.

Certain cancers represent yet another kind of swollen tissues. Once cancer has reached the tumor stage, where lumps of cancerous tissues are detectable either directly through touch and vision or indirectly with the aid of MRI and CAT scanners, the principal treatment is surgical. The victim is operated on and the tumor cut out of the body. Frequently, the location and size of the tumor are such that surgical removal results in a severe impairment to the patient's body and lifestyle. For example, surgical removal of a large tumor in a femur frequently results in an amputation.

The operations for surgically removing tumors are nearly universally open incision type operations. These operations are naturally debilitating and require extensive post surgical care. For these reasons, the costs of conventional open incision surgery are enormous.

Although minimally invasive procedures such as laparoscopic or thoracoscopic surgery have increased at geometric rates in frequency of performance, minimally invasive surgery for the treatment of cancer has not been employed. Of course, other kinds of minimally invasive techniques such as chemotherapy and radiation treatment are widely practiced. However, these techniques have substantial debilitating side effects. Patients must suffer significantly in virtually every case.

Nevertheless, minimally invasive techniques are the future of medicine. Patient trauma and hospitalization time are reduced. In addition, costs and expenses are decreased.

Internal wounds such as perforations of internal organs are also generally treated by open surgery. Such wounds may be the result of traumas. A blunt trauma may cause a rupture, for instance, of the spleen and consequent internal bleeding.

OBJECTS OF THE INVENTION

An object of the present invention is to provide a method for treating swollen tissues including, but not limited to, hemorrhoidal tissues, esophageal or gastric varices, and tumors.

It is a further object of the present invention to provide such a method which is less invasive than conventional open-incision surgical techniques.

It is another object of the present invention to provide such a method which is less expensive than one or more conventional techniques.

A more specific object of the present invention is to provide a treatment technique which is of little danger to the patient.

A related object of the present invention is to provide an associated device or assembly for treating such swollen tissues.

These and other objects of the present invention will be apparent from the drawings and descriptions herein. It is to be noted that any one of the above objects may be attained in one or more embodiment of the invention disclosed herein. No one embodiment need attain all of the objects of the invention.

SUMMARY OF THE INVENTION

A medical treatment method comprises, in accordance with the present invention, injecting at least one first magnetic element into organic tissues of a patient on one side of a feature to be closed or collapsed, injecting at least one second magnetic element into the organic tissues of the patient on an opposite side of the feature to be closed or collapsed, and, by virtue of a magnetic attraction between the first magnetic element and the second magnetic element, drawing the organic tissues of the patient together to close or collapse the feature.

In accordance with another aspect of the present invention, the feature to be treated by the method includes a blood vessel. The treatment technique in this circumstance serves in part to constrict the blood vessel. Other tissues about the blood vessel may also be clamped or collapsed owing to the magnetic attraction between the injected elements. For instance, where the blood vessel is in esophageal varices, the drawing of the organic tissues of the patient together includes a constricting or reducing of the varices. Thus, in one simple procedure, the esophagus is opened and the blood vessels in the varices are closed off, preventing bleeding into the digestive tract.

A procedure for constricting swollen internal tissues in accordance with the present invention is preferably executed in a minimally invasive manner. Thus, where the swollen target tissues are esophageal varices, an endoscope is inserted into the patient's esophagus and the magnetic elements are ejected from a biopsy channel of the endoscope. The optics of the endoscope are used to visually detect the varices and select a point of entry on the varices for the magnetic elements.

Where target swollen tissues are a hemorrhoid, the drawing of the organic tissues of the patient together result in a size reduction of the hemorrhoid, as well as a constricting of one or more blood vessels of the hemorrhoid.

The organic tissues into which the magnetic elements are injected may be a tumor. In that case, the drawing together of the tissues entails an interrupting of a blood supply of the tumor. The attraction between the magnetic elements serves to at least partially collapse the blood vessels which feed the tumor. In many cases, the magnetic elements may be injected into a tumor via a minimally invasive procedure. A needle may be used to inject the magnetic elements.

In general, where the target tissues are swollen tissues such as varices, a tumor, or hemorrhoids, it is not necessary to identify and locate particular blood vessels which are to be closed or collapsed. Instead, the magnetic elements are injected into the target tissues in such numbers and with such a density that blood vessels located in the target tissues are naturally constricted by the movement of the injected magnetic elements under the magnetic attractive forces.

In some cases, the target is an identifiable wound or opening. In that case, a permanent magnet is injected into tissues on one side of the wound or opening, while another permanent magnet or one or more magnetizable particles (generally metallic) are injected on an opposite side of the wound or opening. The magnetic attraction results in a constricting of the tissues and a closure of the wound or opening.

Accordingly, it is contemplated that at least one of the magnetic elements is a permanent magnet. The other magnetic elements may include one or more permanently magnetized particles, as well as one or more magnetizable particles. The magnetizable particles may be made of a metal such as iron or steel or may be made of a polymeric material in which magnetic atoms are embedded. The magnetic elements may be formed at one end with a point for facilitating entry into the target tissues and are of a suitable size for exerting a compressive force on the target tissues. In some case, metal filings may be used. Filings generally have sharp points or edges facilitating injection into organic tissues.

It is to be noted that where the magnetic elements or particles are injected into digestive tract tissues, a subsequent dislodgement of the particles merely results in their being flushed from the body with excreted materials.

A medical treatment device or instrument comprises, in accordance with the present invention, an elongate tube housing a plurality of magnetic elements, and a pressure applicator operatively connected to the tube for exerting a force on the magnetic elements to eject the magnetic elements from an end of the tube into organic tissues of a patient.

The pressure applicator may simply be a plunger. Alternatively or additionally, the magnetic elements may be disposed in a matrix of a biocompatible or bioabsorbable gel. Pressure placed on the gel from a handle or proximal end of the instrument, e.g., via a plunger or pump, forces the gel and the ensconced magnetic elements from the free or distal end of the instrument into the target tissues. Before the ejection of the magnetic elements from the tube of the treatment device, the free or distal end of the instrument is positioned in contact with the target tissues. Generally, this contact is with only an external surface of the target tissues. However, it is also possible for the distal end of the instrument to be partially inserted into the target tissues.

In a particular embodiment of a medical treatment device in accordance with the present invention, the device includes a pair of attached parallel tubes, with unmagnetized metal particles disposed in one of the tubes and permanently magnetized magnetic elements disposed in the other tube. Each tube is provided with a respective pressure applicator for exerting a force on the respective magnetic elements to eject them into organic tissues of the patient. In this embodiment, the permanently magnetized magnetic elements may be disposed in the respective tube so that like poles of the permanently magnetized magnetic elements face one another.

The present invention provides, inter alia, a method for treating swollen tissues including, but not limited to, hemorrhoidal tissues, esophageal or gastric varices, and tumors. This method is less invasive and less expensive than conventional open-incision surgical techniques.

BRIEF DESCRIPTION OF THE DRAWINGS

FIG. 3 is a schematic partial cross-sectional view of a patient's abdomen, showing a step in a laparoscopic procedure for destroying a liver tumor in accordance with the present invention.

FIG. 4 is a schematic view of a tumor, showing a step in an intravascular procedure for destroying the tumor in accordance with the invention.

FIG. 5 is a schematic longitudinal cross-sectional view of a tubular instrument in accordance with the present invention, for performing a medical treatment method pursuant to the invention.

FIG. 6 is a schematic longitudinal cross-sectional view of another tubular instrument in accordance with the present invention, for performing a medical treatment method pursuant to the invention.

FIG. 7 is a schematic longitudinal cross-sectional view of a further tubular instrument in accordance with the present invention, for performing a medical treatment method pursuant to the invention.

DESCRIPTION OF PREFERRED EMBODIMENTS

Figure 1A:
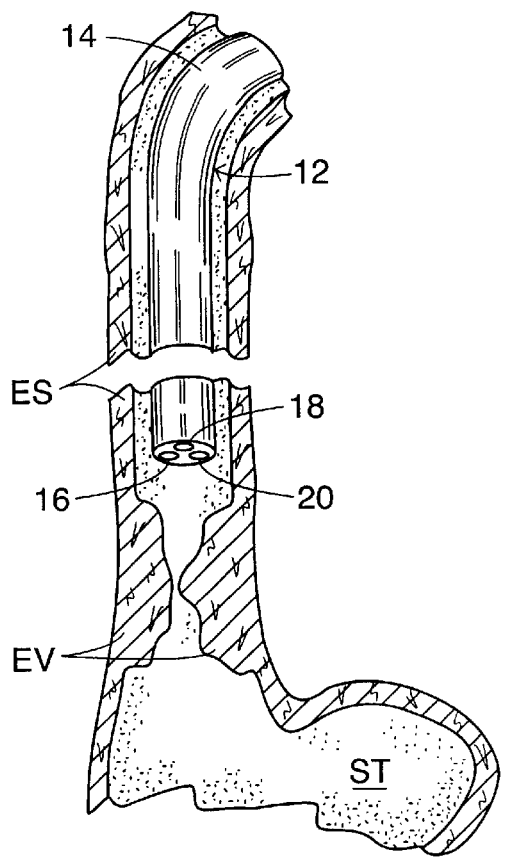
FIGS. 1A–1C are schematic cross-sectional views of an esophagus with varices, showing successive steps in an endoscopic procedure for reducing the varices in accordance with the present invention.
Figure 1C:
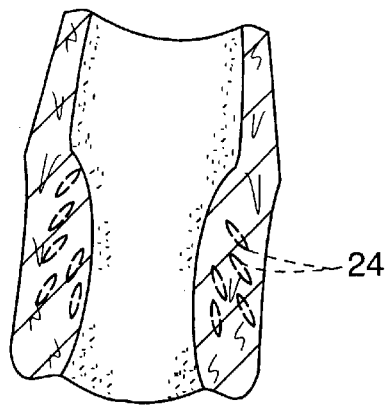

FIG. 1A shows an esophagus ES which is afflicted with varices EV at a lower end, near the stomach ST. The location and size of the varices EV are detected visually with the aid of an endoscope 12. Endoscope 12 includes a flexible insertion member 14 provided with a first light guide (not shown) having an outlet 16 for guiding electromagnetic radiation into esophagus ES to illuminate the internal tissues of the esophagus, including varices EV. Endoscope 12 is further provided with a lens 18 for focusing reflected light onto a charge-coupled device (not shown) or the input end of an optical fiber bundle (not shown).

Figure 1B:
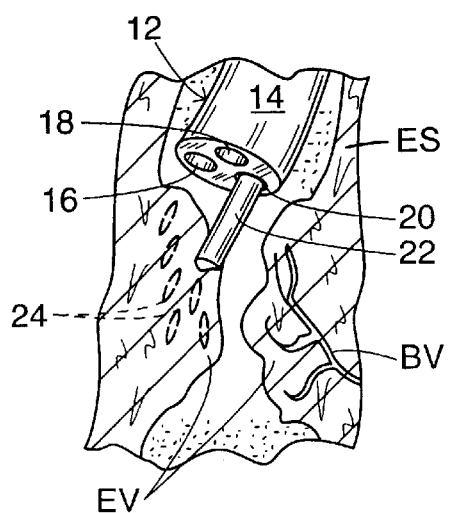
Figure 2B:
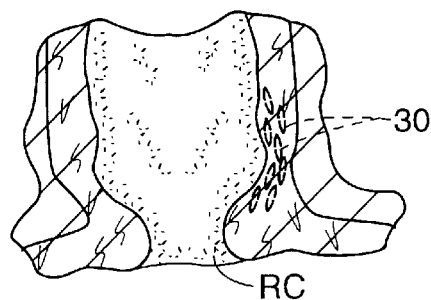
Figure 8:
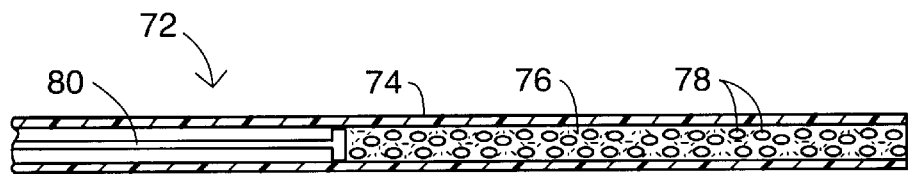
FIG. 8 is a schematic longitudinal cross-sectional view of yet another tubular instrument in accordance with the present invention, for performing a medical treatment method pursuant to the invention.

Endoscope 12 has a biopsy channel 20 through which a tubular instrument 22 is deployed so that a distal end portion of the instrument (not separately labeled) is positionable in contact with the varices EV, as shown in FIG. 1B. Instrument 22 is operated to inject a plurality of magnetic particles 24 into the varices EV. One or more of the magnetic particles 24 are permanent magnets. Others of the magnetic particles 24 may be made of magnetizable material such as iron or steel. Upon injection of particles 24 into varices EV, magnetic attraction causes the particles to approach one another and concomitantly constrict or collapse the tissues of the varices EV. This magnetically implemented constriction entails a closure of blood vessels BV (FIG. 1B) in the varices. The closure is sufficient to induce clotting and a permanent closure of the blood vessels. Thus, the varices EV are not likely to reappear, at least not in the same location in the esophagus ES.

Figure 2A:
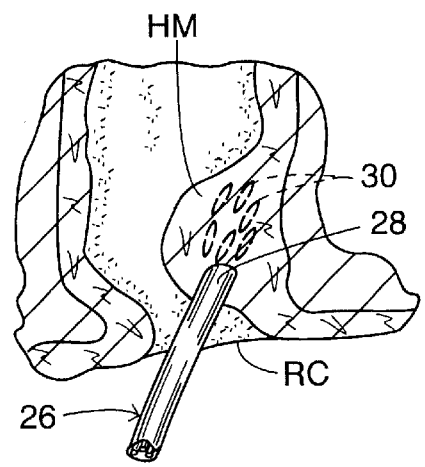
FIGS. 2A and 2B are schematic cross-sectional views of an anus with hemorrhoids, showing successive steps in an endoscopic procedure for shrinking the hemorrhoids in accordance with the present invention.

As illustrated in FIG. 2A, a free or distal end 28 of a tubular medical instrument 26 is inserted into a rectum RC and placed in contact with a hemorrhoid HM. The instrument 26 is operated to inject a plurality of magnetic elements 30 into the hemorrhoid HM. One or more of the magnetic elements 30 are permanent magnets. Other magnetic elements 30 may be made of magnetizable material such as iron or steel. Under the influence of magnetic attraction, elements 30 approach one another upon injection thereof into hemorrhoid HM and thus result in a constriction or internal clamping of the hemorrhoidal tissues.

As depicted in FIG. 3, a distal end portion 32 of a tubular laparoscopic instrument 34 is inserted through a cannula or trocar sleeve 36 into an abdominal cavity AC of a patient. Distal end portion 32 of instrument 34 is further inserted into an internal organ such as the liver LV of the patient so that the distal tip of the instrument is placed into effective contact with a tumor TM inside the organ. Instrument 34 is operated to inject a plurality of magnetic elements 38 into tumor TM. As described above, injection of elements 38 into tumor TM results in a contraction of the tumor and an at least partial constriction of blood vessels (not shown) of the tumor. The constriction of the blood vessels in the tumor TM induces clotting and a permanent closure of the blood vessels. Without an adequate blood supply, the tumor TM dies.

FIG. 4 shows an alternate procedure for destroying a tumor MT having a blood supply including an artery AR and a vein VN. A distal end portion 40 of a flexible tubular medical instrument 42 in inserted through artery AR (or vein VN) into tumor MT. Then instrument 42 is operated to inject magnetic particles 44 into tumor MT, resulting in an at least partial collapse of the tumor's blood vessels and a clotting leading to tumor destruction.

The laparoscopic procedure of FIG. 3 and the intravascular procedure of FIG. 4 are performed using well-established laparoscopic and radiographic techniques. Alternatively, the deployment of laparoscopic instrument 34 and intravascular instrument 42 may be implemented under observation mediated by ultrasound. Such techniques are described in U.S. Pat. Nos. 5,871,446, 6,023,632, 6,106,463, and 6,139,499. Alternatively or additionally, the operation of instruments 34 and 42 may be robotically mediated, under remote control, as described in U.S. Pat. Nos. 5,217,003, 5,217,453, and 5,368,015.

Instruments 22, 26, 34, and 42 may take a form described now with reference to FIGS. 5–8. As depicted in FIG. 5, a medical treatment instrument 46 includes a rigid or flexible tubular member 48 with a lumen 50 carrying a plurality of permanent magnets 52. Magnets 52 are disposed end to end, with like magnetic poles (S, N) facing one another to thereby space the magnets 52 along lumen 50. A pressure applicator in the form of a plunger 54 is provided for ejecting magnets 52 from a distal tip 56 of tubular member 48. Alternative devices for the application of an ejection force to the array of magnets 52 include pumps, syringes, and other hydrostatic fluid injectors (none shown). In such a case, magnets 52 are disposed in lumen 50 in a biocompatible fluid such as saline or gel. Magnets 52 are optionally formed at a leading end with a point or edge 58 for facilitating the insertion of the magnets into organic tissues of a patient during a medical treatment procedure.

An instrument 60 shown in FIG. 6 includes a rigid or flexible tubular member 62 having a lumen 64 carrying a multiplicity of magnetizable elements 66 such a metal filings. A plunger 68 is slidably disposed in a proximal portion of lumen 64 for applying an ejection pressure to magnetizable elements 66. The function of plunger 68 may be alternatively performed by a pump, a syringe, or some other pressure application device such as a shifting sleeve magnetically linked to filings 66.

Instruments 46 and 62 (FIGS. 5 and 6) may be used successively in the same medical operation, for example, to inject one or more magnets 52 into a body of organic tissues and subsequently to inject a plurality of metal filings 66.

FIG. 7 depicts an instrument 70 representing a combination of the instruments of FIGS. 5 and 6. The same reference numerals are used in FIG. 7 to designate the same components in FIGS. 5 and 6. Tubular members 48 and 62 are connected to one another so that they extend parallel to one another. The distal tips 56 and 69 of tubular members 48 and 62 may be coplanar as shown in FIG. 7 or longitudinally spaced. Instrument 70 facilitates a single deployment procedure and simultaneous or temporally staggered ejection of magnets 52 and filings 66. Instrument 70 is particularly, but not exclusively, adapted for use in the procedures of FIGS. 2A and 3.

Another instrument 72 (FIG. 8) for executing a magnet injection medical procedure includes a rigid or flexible tubular member 74 carrying a fluid or gel matrix 76 in which a plurality of magnetic particles 78 are embedded. A plunger 80 or other pressure application device is operatively connected to tubular member 74 for forcibly ejecting matrix 76 and particles 78 to place the particles in a target tissue mass.

Figure 9:
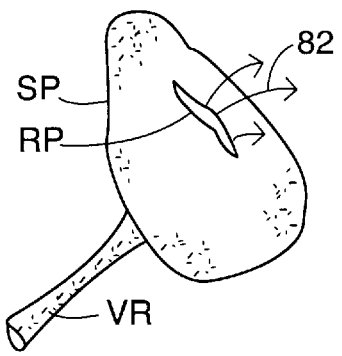
FIG. 9 is a schematic perspective view of an internal organ such as a spleen, showing a bleeding rupture in the organ.
Figure 10:
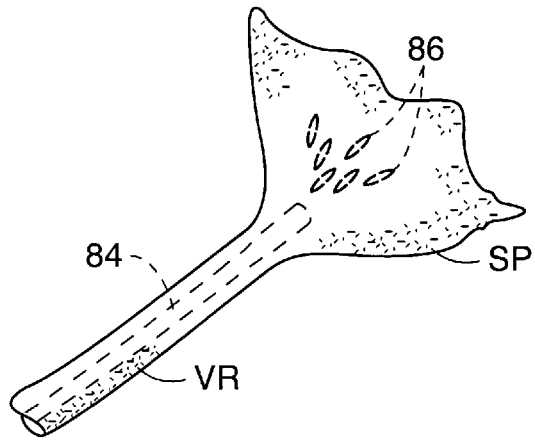
FIG. 10 is a schematic partial perspective view, on a larger scale, of the ruptured organ of FIG. 9, showing an intravascularly implemented procedure for arresting blood flow in accordance with the present invention.

As shown in FIG. 9, an internal organ such as a spleen SP may be afflicted with a wound or rupture RP inflicted, for example, by a blunt trauma to the person of the individual patient. The rupture RP results in bleeding, indicated by arrows 82. As illustrated in FIG. 10, a minimally invasive surgical treatment of the injured organ SP entails the insertion of a distal end portion (not separately designated) of a tubular member 84 into the organ, for instance, intravascularly through a vein or artery VR supplying the organ. A plurality of magnetic elements or particles 86 are ejected from distal end of the inserted tubular member 84 into the injured organ SP. The magnetic particles 86 are injected into the injured organ SP at a location which results in a collapsing or constriction of a blood supply to the ruptured portion of the organ SP, thereby arresting the bleeding 82.

Figure 11A:
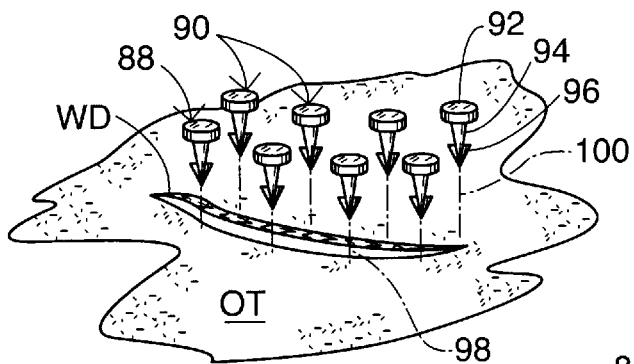
FIGS. 11A and 11B are schematic perspective views of a wound, showing successive steps in a wound-closure method in accordance with the present invention.
Figure 11B:
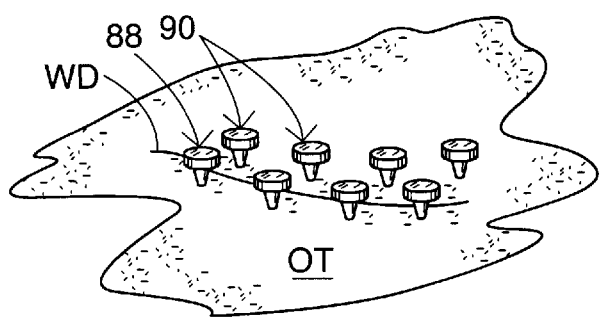

FIGS. 11A and 11B depict successive steps in a wound closure procedure utilizing two groups of magnetic tacks 88 and 90. Tacks 88 and 90 each includes a head 92 and a stem 94 provided with barbs 96 for preventing tack removal. Stems 94 of tacks 88 are inserted into organic tissues OT on one side of a wound WD, as indicated by dot-dash insertion lines 98. Similarly, stems 94 of tacks 90 are inserted into organic tissues OT on an opposite side of wound WD, as indicated by dot-dash insertion lines 100. Tacks 88 and/or 90 are permanently magnetized. Those tacks which are not magnetized are made of a magnetizable material. Magnetic attraction between tacks 88 and tacks 90 cause tacks 88 and 90 to compress the intervening tissues OT and close wound WD. Tacks 88 and 90 may be inserted in an open surgical procedure or alternatively in a minimally invasive operation using a tubular tack applicator (not shown).

Figure 12A:
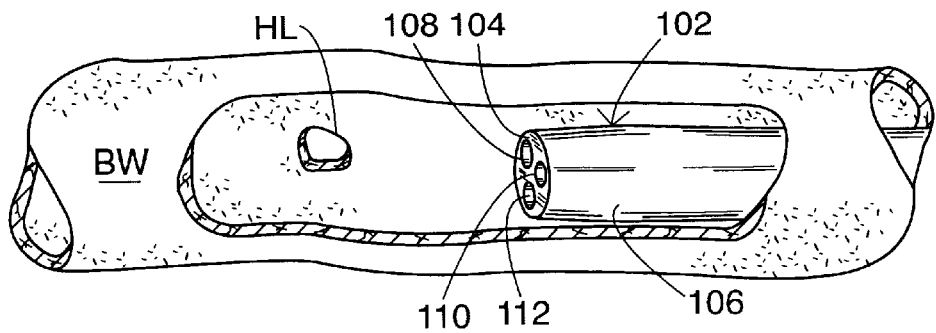
FIGS. 12A through 12D are schematic side elevational views of a colon, partially broken away to show successive steps in an endoscopically implemented hole-closure procedure in accordance with the present invention.
Figure 12B:
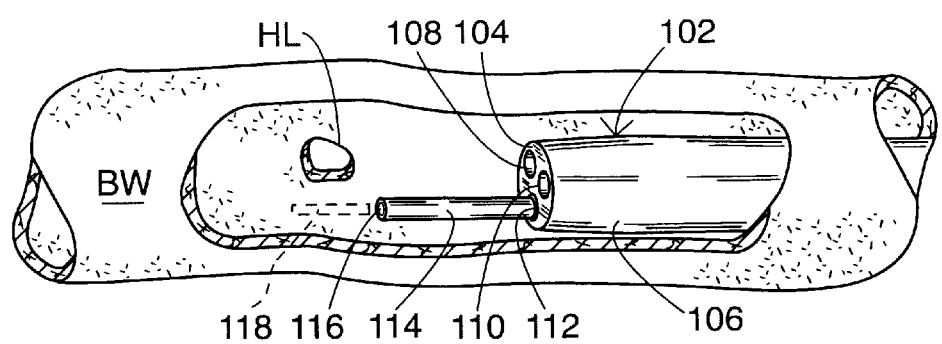
Figure 12C:
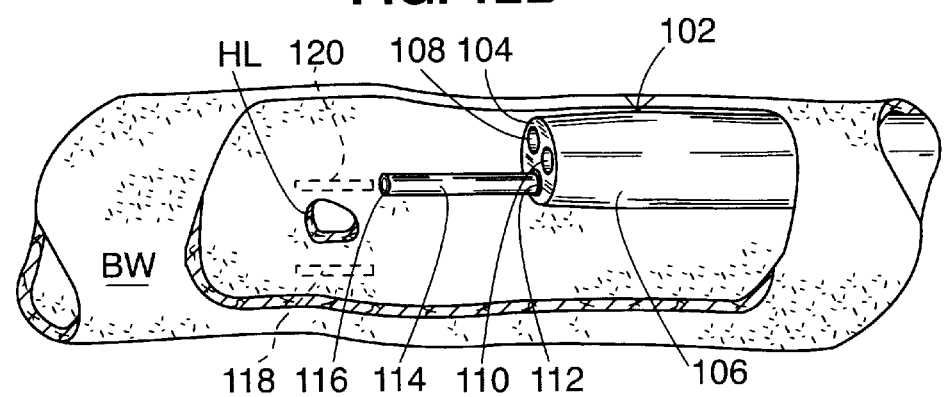
Figure 12D:
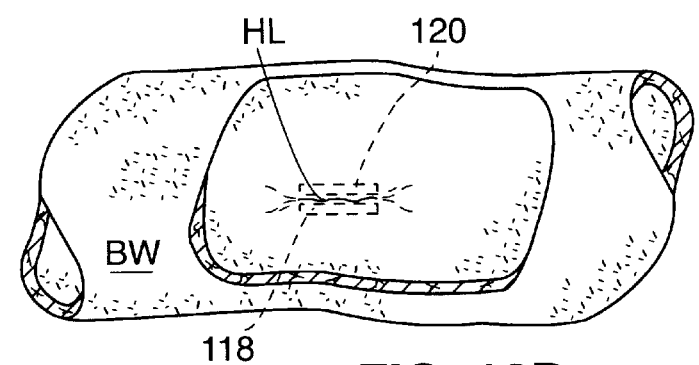

FIGS. 12A through 12D depict successive steps in an endoscopic procedure for closing a hole HL in a wall of an internal organ such as a bowel BW. As indicated in FIG. 12A, hole HL is detected via an endoscope 102 which is provided at a distal end 104 of a flexible shaft or insertion member 106 with an illumination port 108, a lens 110, and a biopsy channel mouth 112. To close hole HL, a distal end portion of a tubular instrument 114 is ejected from biopsy channel mouth 112. Upon a placement of a distal tip 116 of instrument 114 in contact with the wall of bowel BW proximate to hole HL, instrument 114 is operated to inject a magnetic element 118 into the bowel wall. Endoscope insertion member 106 is subsequently manipulated to position the distal tip 116 of instrument 114 in contact with the wall of bowel BW on an opposite side of hole HL. At that juncture, another magnetic element 120 is injected into the wall of bowel BW as shown in FIG. 12C. An attractive magnetic force between elements 118 and 120 causes them to approach one another and thereby close hole HL, as indicated in FIG. 12D.

Figure 13A:
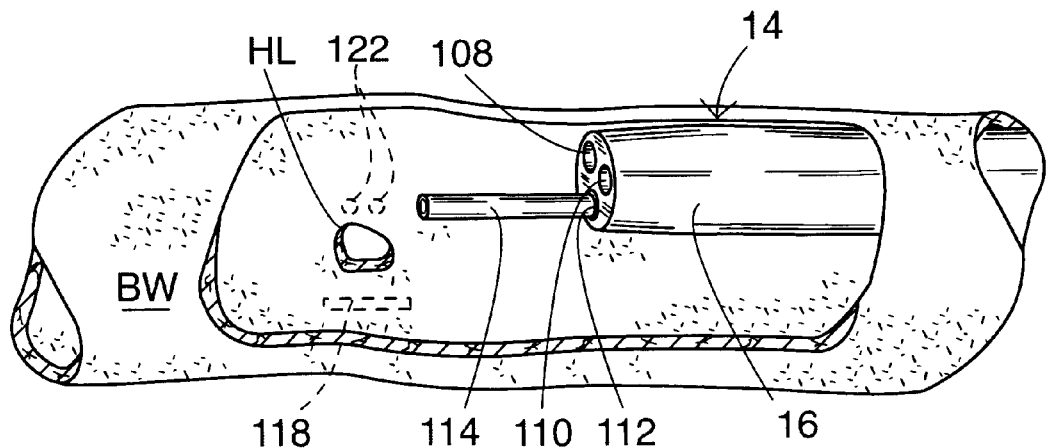
FIGS. 13A through 13C are schematic side elevational views similar to FIGS. 12A–12D, showing successive steps in an alternative hole-closure procedure in accordance with the present invention.
Figure 13B:
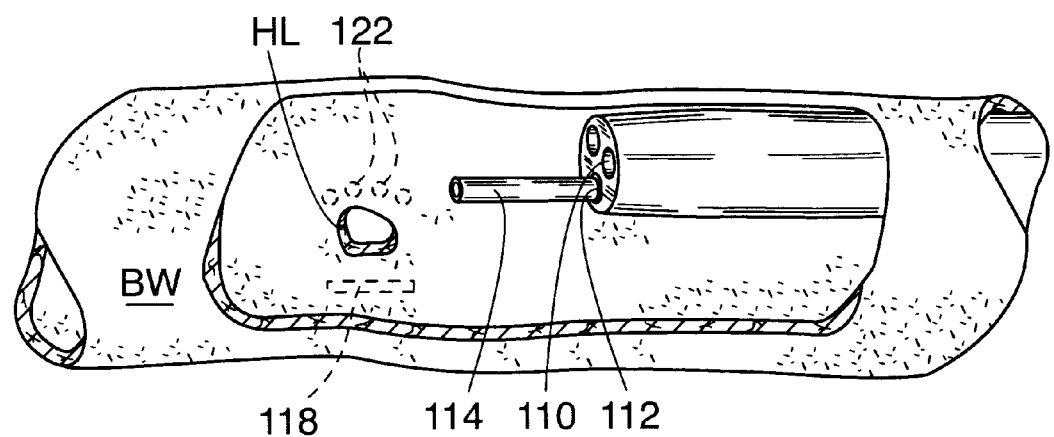
Figure 13C:
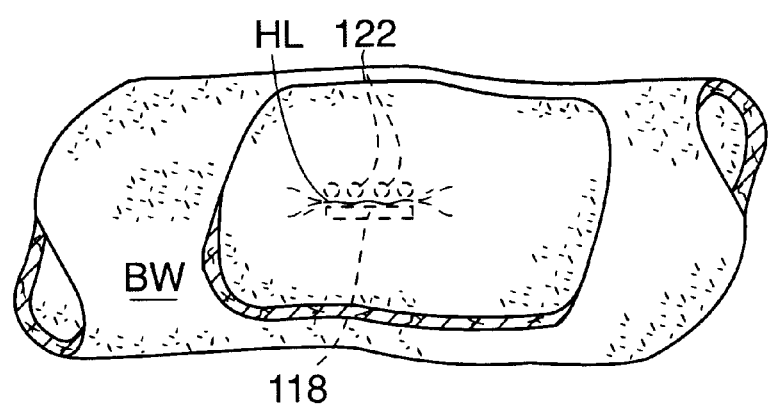

FIGS. 13A through 13C depict successive steps in a modification of the procedure of FIGS. 12A–12D, in which elongate magnetic element 120 is replaced by a group of smaller magnetic elements 122. Elements 122 are injected in sequence into the wall of bowel BW at spaced points on a side of hole HL opposite magnetic element 118. Elements 122 are substantially spherical and easily rotate inside the tissues of bowel BW, thereby facilitating registration or alignment of opposite magnetic poles on element 118 on the one hand and elements 122 on the other hand.

Figure 14A:
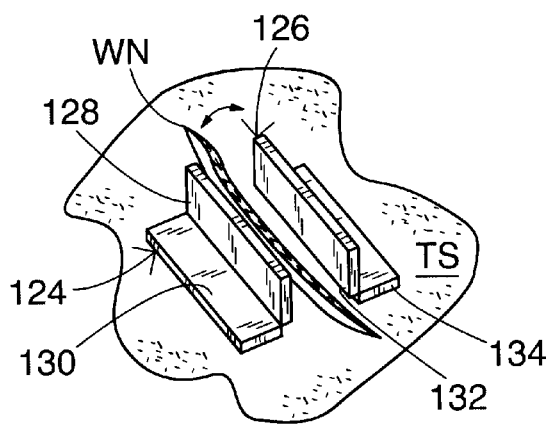
FIGS. 14A through 14C are schematic perspective views showing another procedure for closing a wound in accordance with the present invention.
Figure 14B:
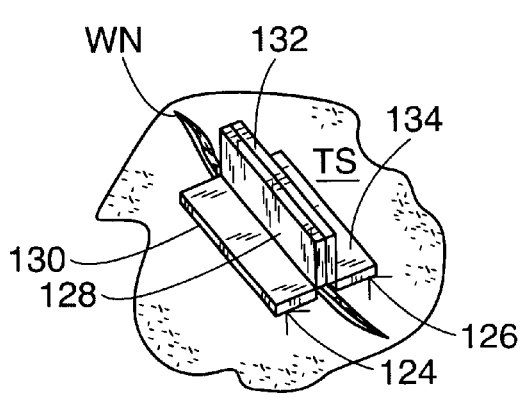
Figure 14C:
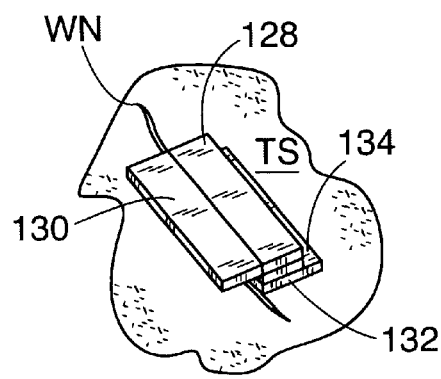

FIGS. 14A through 14C depict successive steps in a procedure for closing a wound WN utilizing a pair of closure components 124 and 126. Closure component 124 includes a magnetic plate 128 hingedly secured to an adhesive strip 130. Similarly, closure component 126 comprises a magnetic plate 132 pivotably attached to an adhesive strip 134. As indicated in FIG. 14A, adhesive strips 130 and 134 are first attached to a tissue surface TS on opposite sides of wound WN. Plates 128 and 132 are angled with respect to their respective adhesive strips 130 and 134 so that the plates face one another across wound WN. Plates 128 and 132 are magnetized so that the facing sides of the plates exhibit opposite magnetic poles. Magnetic attraction causes plates 128 and 132 to clamp to one another, as illustrated in FIG. 14B, thereby closing wound WN. Plates 128 and 132 are pivoted, as illustrated in FIG. 14C, to flatten the plates against tissue surface TS.

The various magnetic elements disclosed herein, including particles or filings 24, 38, 44, 66, 78, 86, tacks 88 and 90, elements 118, 120, 122, and plates 128 and 132, as well as adhesive strips 130 and 134, may be made of a bioabsorbable material with embedded or dispersed ferromagnetic atoms.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical treatment method comprising:
   injecting at least one first magnetic element into organic tissues of a patient on one side of a feature to be closed or collapsed;
   injecting at least one second magnetic element into the organic tissues of the patient on an opposite side of the feature to be closed or collapsed; and
   by virtue of a magnetic attraction between said first magnetic element and said second magnetic element, drawing the organic tissues of the patient together to close or collapse said feature.

2. The method defined in claim 1 wherein said feature includes a blood vessel.

3. The method defined in claim 2 wherein said blood vessel is in esophageal varices, the drawing of the organic tissues of the patient together including a constricting or reducing of the varices.

4. The method defined in claim 3 wherein the inserting of said first magnetic element and said second magnetic element into the esophageal tissues includes inserting an endoscope into the patient's esophagus and ejecting said first magnetic element and said second magnetic element from a biopsy channel of said endoscope.

5. The method defined in claim 2 wherein said blood vessel is in a hemorrhoid, the drawing of the organic tissues of the patient together including a constricting or reducing of the hemorrhoid.

6. The method defined in claim 2 wherein said blood vessel is in a tumor, the drawing of the organic tissues of the patient together including an interrupting of a blood supply of the tumor.

7. The method defined in claim 1 wherein at least one of said first magnetic element and said second magnetic element is a permanent magnet.

8. The method defined in claim 1 wherein at least one of said first magnetic element and said second magnetic element is a particle having a pointed end.

9. The method defined in claim 1 wherein said one of said first magnetic element and said second magnetic element is a metal filing, the injecting of said one of said first magnetic element and said second magnetic element including injecting a plethora of magnetic filings into the tissues of the patient.

10. The method defined in claim 1 wherein said feature is a wound or opening in the organic tissues of the patient.

11. The method defined in claim 1 wherein the inserting of said first magnetic element and said second magnetic element includes inserting an endoscope into the patient and ejecting said first magnetic element and said second magnetic element from a biopsy channel of said endoscope.

12. The method defined in claim 1 wherein said first magnetic element and said second magnetic element are included in a multiplicity of magnetic particles injected into the tissues of the patient.

13. A medical treatment device comprising:
    an elongate tube housing a plurality of magnetic elements in the form of unmagnetized metal particles, said tube being one of a pair of parallel tubes connected to one another, another one of said tubes housing a plurality of permanently magnetized magnetic elements;
    a pressure applicator operatively connected to said tube for exerting a force on said magnetic particles to eject said magnetic particles from an end of said tube into organic tissues of a patient; and
    an additional pressure applicator operatively connected to said another one of said tubes for exerting a force on said permanently magnetized magnetic elements to eject said permanently magnetized magnetic elements from an end of said another one of said tubes into organic tissues of the patient.

14. The device defined in claim 13 wherein said permanently magnetized magnetic elements are disposed in said another one of said tubes so that like poles on said permanently magnetized magnetic elements face one another.

15. The device defined in claim 13 wherein said additional pressure applicator includes a plunger.

16. The device defined in claim 13 wherein the pressure applicator for ejecting said metal particles includes a plunger.

17. A medical closure method comprising:
    providing a medical treatment assembly including two connectors each comprising an adhesive portion and a magnetic part;
    fastening the adhesive portion of each of said connectors to a tissue surface on opposite sides of a wound to be closed; and
    orienting the magnetic part of each of said connectors to face one another across said wound so that the connectors become magnetically coupled to one another and close said wound.

* * * * *